(12) United States Patent
Ramos (10) Patent No.: US 8,524,897 B2
(45) Date of Patent: Sep. 3, 2013

(54) CRYSTALLINE OXAZINE DERIVATIVE

(75) Inventor: Rita Ramos, Allschwil (CH)

(73) Assignee: Novartis AG, Basel (CH)

( * ) Notice: Subject to any disclaimer, the term of this patent is extended or adjusted under 35 U.S.C. 154(b) by 61 days.

(21) Appl. No.: 13/347,067

(22) Filed: Jan. 10, 2012

(65) Prior Publication Data

US 2012/0178745 A1  Jul. 12, 2012

Related U.S. Application Data (60) Provisional application No. 61/432,058, filed on Jan. 12, 2011, provisional application No. 61/435,088, filed on Jan. 21, 2011.

(51) Int. Cl.
*C07D 413/12* (2006.01)

(52) U.S. Cl.
USPC .......................................... 544/98; 546/282.1

(58) Field of Classification Search
USPC ................................. 514/228.8; 544/106, 98
See application file for complete search history.

(56) References Cited

U.S. PATENT DOCUMENTS

| | | |
|---|---|---|
| 5,691,336 A | 11/1997 | Dorn et al. |
| 7,642,272 B2 | 1/2010 | Shankar et al. |
| 7,745,438 B2 | 6/2010 | Broughton et al. |
| 7,888,374 B2 | 2/2011 | Liu et al. |
| 2007/0149547 A1 | 6/2007 | Bonnefous et al. |
| 2009/0082560 A1 | 3/2009 | Kobayashi et al. |
| 2009/0209755 A1 | 8/2009 | Suzuki et al. |
| 2010/0075957 A1 | 3/2010 | Tamura et al. |
| 2010/0137336 A1 | 6/2010 | Bolea |
| 2010/0197688 A1 | 8/2010 | Nantermet et al. |
| 2011/0021520 A1 | 1/2011 | Badiger et al. |
| 2011/0190279 A1 | 8/2011 | Hori et al. |
| 2011/0237576 A1 | 9/2011 | Yonesawa et al. |
| 2012/0238560 A1 | 9/2012 | Holzer et al. |

FOREIGN PATENT DOCUMENTS

| | | |
|---|---|---|
| EP | 2 151 435 A1 | 2/2010 |
| WO | 2008/106692 A1 | 9/2008 |
| WO | 2009/010454 | 1/2009 |
| WO | 2010/007756 A1 | 1/2010 |
| WO | 2010/070502 A2 | 6/2010 |
| WO | 2010/128058 A1 | 11/2010 |
| WO | 2011/009943 A1 | 1/2011 |
| WO | 2011/020806 A1 | 2/2011 |
| WO | 2011/058763 A1 | 5/2011 |
| WO | 2011/069934 A1 | 6/2011 |
| WO | 2011/070029 A1 | 6/2011 |
| WO | 2011/071135 A1 | 6/2011 |
| WO | 2011/077726 A1 | 6/2011 |
| WO | 2011/080176 A1 | 7/2011 |
| WO | 2011/138293 A1 | 11/2011 |
| WO | 2011/154374 A1 | 12/2011 |
| WO | 2011/154431 A1 | 12/2011 |
| WO | 2012/006953 A1 | 1/2012 |

OTHER PUBLICATIONS

U.S. Appl. No. 13/414,440 "Oxazine Derivatives and their Use in the Treatment of Neurological Disorders" filed in the name of NOVARTIS AG on Apr. 4, 2012.
U.S. Appl. No. 13/414,483 "Oxazine Derivatives and their Use in the Treatment of Neurological Disorders" filed in the name of NOVARTIS AG on Apr. 4, 2012.
U.S. Appl. No. 13/518,907, filed Dec. 22, 2010.
Copending U.S. Appl. No. 13/255,036, filed Feb. 10, 2012.
Patani et al., Bioisosterism: A Rational Approach in Drug Design, Chem. Rev., 96:3147-3176 (1996).
Non-Final Rejection dated Jan. 30, 2013 in U.S. Appl. No. 13/518,907.

*Primary Examiner* — Joseph K. McKane
*Assistant Examiner* — Amanda L Aguirre
(74) *Attorney, Agent, or Firm* — Joshua Roth (57) ABSTRACT

The invention relates to 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form, to its preparation, its medical use and to medicaments comprising said compound in crystalline form.

9 Claims, 3 Drawing Sheets

CRYSTALLINE OXAZINE DERIVATIVE

FIELD OF INDUSTRIAL APPLICABILITY

The present disclosure generally relates to crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide. The present disclosure also generally relates to a pharmaceutical composition comprising crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide, as well of methods of using the crystalline form in the treatment of Alzheimer's Disease, and methods for obtaining such crystalline material.

BACKGROUND

Alzheimer's Disease is a devastating neurodegenerative disorder. Its sporadic forms affect an elderly population (sharp increase in incidence at >75 years of age), in addition, there are various familial forms with an onset of the disease in the fourth or fifth decade of life. Pathologically, it is characterized by the presence of extracellular senile plaques, and intracellular neurofibrillar tangles in patient's brains. The core constituent of the senile plaques are small, 4 kDa amyloid peptides. They are generated by the proteolytic processing of a large transmembrane protein, amyloid precursor protein (APP). Cleavage of APP by beta-secretase (BACE-1) releases the soluble APP-beta fragment, while the 99-amino acid long C-terminus remains tethered to the membrane. This C-terminal fragment is subsequently proteolytically processed by gamma-secretase (a membrane multi-enzyme complex) to generate amyloid peptides of various length, predominantly 40 and 42 amino acids long (Hardy J, Selkoe D J (2002) Science; 297 (5580):353-356).

If, under pathologic conditions, the generation of these peptides occurs at an increased rate, or if their removal from the brain is disturbed, increased brain amyloid peptide concentrations leads to the formation of oligomers, fibrils and eventually plaques (Farris W, et al (2007) Am. J. Pathol.; 171 (1):241-251). It has been shown, that deposition of amyloid peptides and plaques in the brain is the first measurable event in the pathogenesis of Alzheimers Disease, and that it is the trigger for loss of synapses, synaptic contacts, and neurons (Grimmer T, et al (2009) Neurobiology of Aging; 30 (12): 1902-1909). Brain atrophy caused by massive neuron loss is followed by impairments in cognition, memory, orientation and the ability to perform the tasks of daily living, i.e. clinically manifest dementia (Okello A, et al (2009) Neurology; 73 (10):754-760). BACE-1, also known as Asp2 or Memapsin 2, is a transmembrane aspartic protease highly expressed in neurons. It co-localizes with its substrate APP in Golgi and endocytic compartments (Willem M, Lammich S, Haass C (2009) Semin. Cell Dev. Biol; 20 (2):175-182). Knock-out studies in mice have demonstrated the absence of amyloid peptide formation, while the animals are healthy and fertile (Ohno M, et al (2007) Neurobiol. Dis.; 26 (1):134-145). Genetic ablation of BACE-1 in APP-overexpressing mice has demonstrated absence of plaque formation, and the reversal of cognitive deficits (Ohno M, et al (2004) Neuron; 41 (1): 27-33). BACE-1 levels are elevated in the brains of sporadic Alzheimer's Disease patients (Hampel H, Shen Y (2009) Scand. J. Clin. Lab. Invest.; 69 (1):8-12).

Taken together, these findings suggest that the inhibition of BACE-1 may be a favourable therapeutic strategy for the treatment of Alzheimer's Disease.

SUMMARY OF THE DISCLOSURE

The present invention relates to a novel crystalline oxazine derivative, namely crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide, having BACE inhibitory activity, to its preparation, its medical use and to medicaments comprising said crystalline oxazine derivative.

Crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide offers advantages over the corresponding non-crystalline compound in terms of at least chemical stability and ease of formulation.

DETAILED DESCRIPTION OF THE DISCLOSURE

In a first aspect of the invention, there is therefore provided 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form.

The chemical structure of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide is For the avoidance of doubt, the invention provides crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in free form. The term "free form" refers to the compound per se without salt formation.

In one embodiment of the invention, there is provided crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in substantially pure form.

As used herein, "substantially pure," when used in reference to crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide, means having a purity greater than 90 weight %, including greater than 90, 91, 92, 93, 94, 95, 96, 97, 98, and 99 weight %, and also including equal to about 100 weight % of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide, based on the weight of the compound.

The presence of reaction impurities and/or processing impurities may be determined by analytical techniques known in the art, such as, for example, chromatography, nuclear magnetic resonance spectroscopy, mass spectrometry, or infrared spectroscopy.

In a more focused aspect, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]amide which has an X-ray powder diffraction pattern with at least one, two or three peaks having angle of refraction 2 theta (θ) values selected from 8.3, 9.0, 10.9, 12.9, 13.9, 15.4, 16.2, 17.1, 18.2, and 24.5° when measured using CuK$_α$ radiation, more particularly wherein said values are plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with at least one, two, three or four peaks having angle of refraction 2 theta (θ) values selected from 8.3, 9.0, 10.9, 12.9, 13.9, 15.4, 16.2, 17.1, 18.2, and 24.5° when measured using CuK$_α$ radiation, more particularly wherein said values are plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 8.3° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 9.0° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]amide which has an X-ray powder diffraction pattern with a peak at an angle of refraction 2θ value of 10.9° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 12.9° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 13.9° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 15.4° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 16.2° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 17.1° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]amide which has an X-ray powder diffraction pattern with a peak at an angle of refraction 2θ value of 18.2° when measured using CuK$_α$ radiation, more particularly wherein said value is plus or minus 0.2° 2θ.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern with a peak at an angle of refraction 2θ value of 24.5° when measured using CuK$_α$ radiation, more particularly wherein said value is plus or minus 0.2° 2θ.

Figure 1:
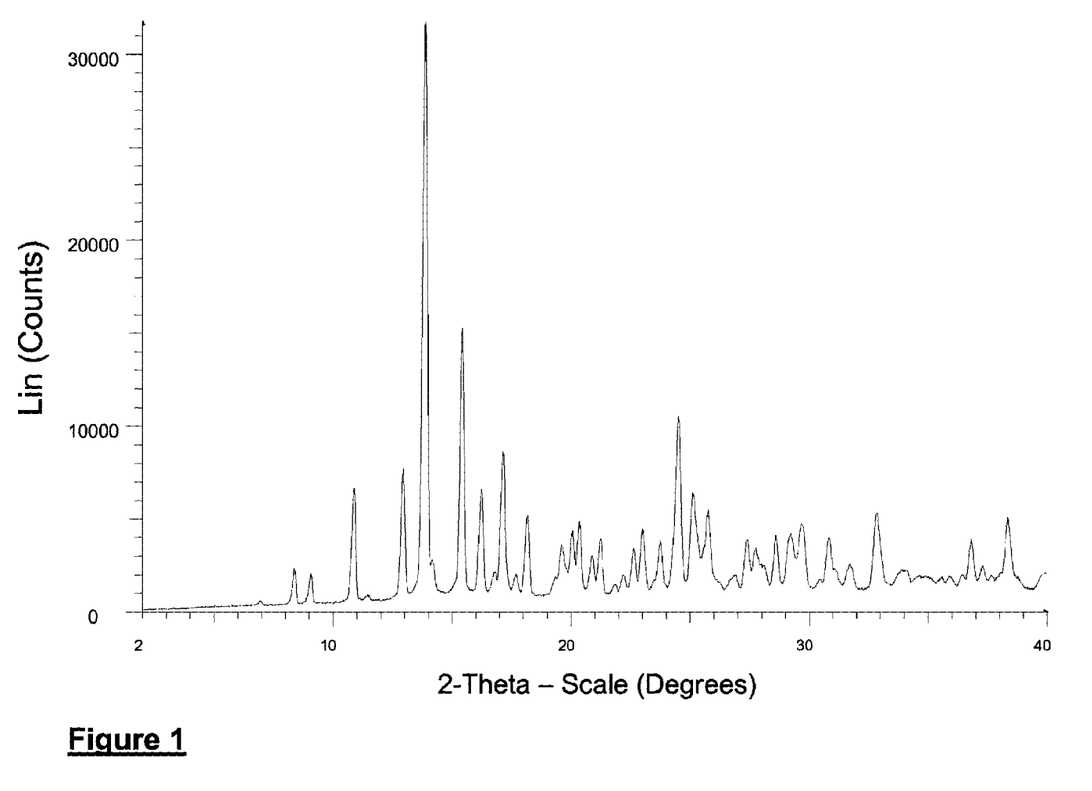
FIG. 1 shows the X-ray powder diffraction pattern for crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]amide when measured using CuK$_\alpha$ radiation.

In one embodiment, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide which has an X-ray powder diffraction pattern substantially the same as the X-ray powder diffraction pattern shown in FIG. 1 when measured using CuK$_α$ radiation. For details see Example 7.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only.

One of ordinary skill in the art will also appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal form of the instant invention is not limited to the crystal form that provides an X-ray diffraction pattern completely identical to the X-ray diffraction pattern depicted in the accompanying FIG. 1 disclosed herein. Any crystal forms that provide X-ray diffraction patterns substantially identical to that disclosed in the accompanying FIG. 1 fall within the scope of the present invention. The ability to ascertain substantial identities of X-ray diffraction patterns is within the purview of one of ordinary skill in the art.

Figure 2:
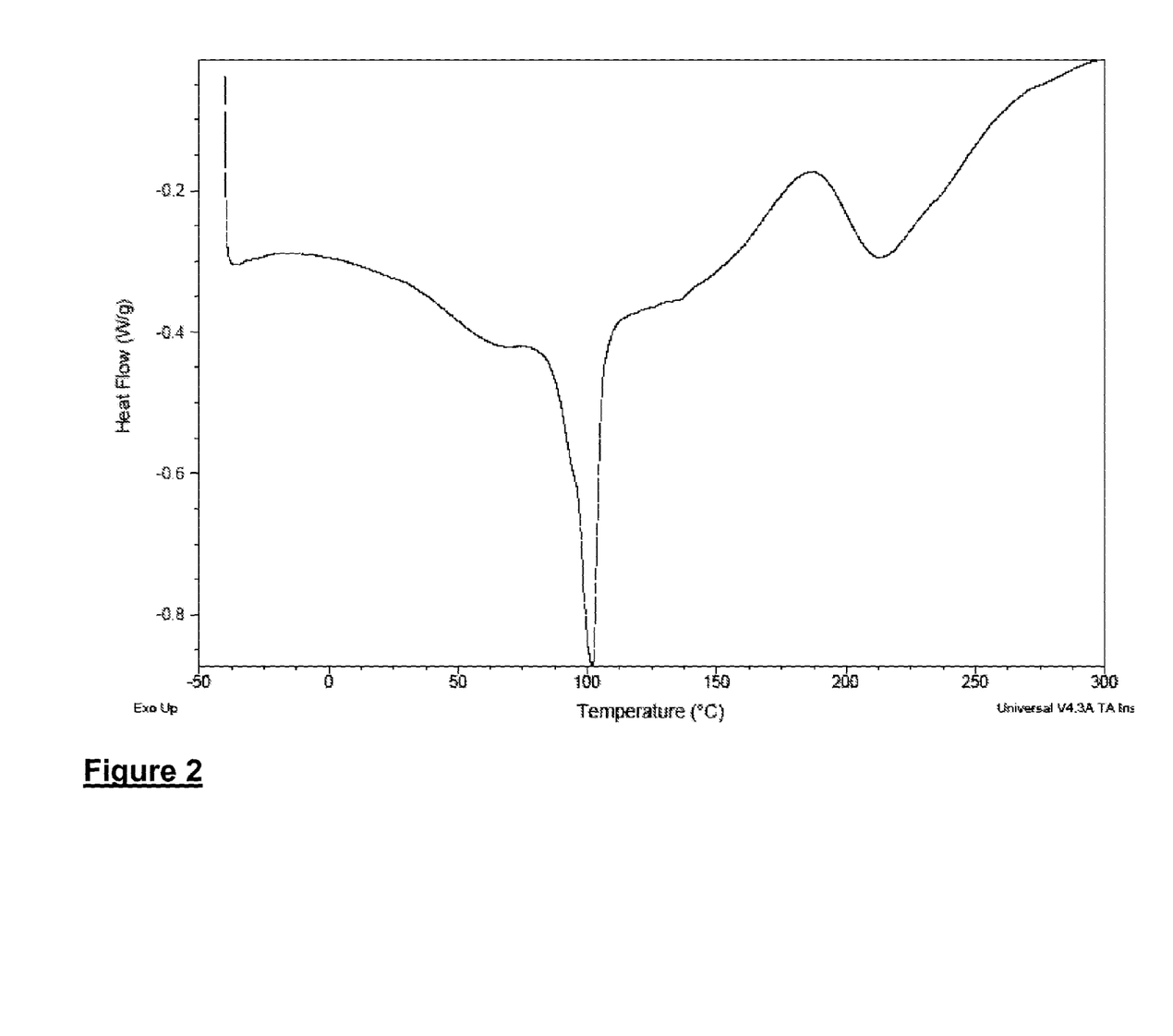
FIG. 2 shows the DSC thermogram for crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide.

In a further aspect of the invention, the invention relates to a crystalline form of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]amide having a differential scanning calorimetry (DSC) thermogram substantially the same as that shown in shown in FIG. 2.

5-Cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form, hereinafter often referred to as "the agent of the invention" or "a compound of the invention", exhibits valuable pharmacological properties, when tested in vitro or in vivo, and may, therefore, be useful in medicaments, in therapy or for use as a research chemical, for example as a tool compound.

For example, the agent of the invention is an inhibitor of aspartic proteases and may be used for the treatment or prevention of a condition, disease or disorder involving processing by such enzymes. Particularly, the agent of the invention inhibits beta-secretase and, thus, the generation of beta-amyloid and the subsequent aggregation into oligomers and fibrils.

The inhibiting properties of the agent of the invention towards proteases can be evaluated in tests as described hereinafter.

Test 1: Inhibition of Human BACE-1

Recombinant BACE-1 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic fluorescence-quenched peptide substrate, derived from the sequence of APP and containing a suitable fluorophore-quencher pair, is added to a final concentration of 1 to 5 μM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-1 activity as a function of the test compound concentration.

Test 2: Inhibition of Human BACE-2

Recombinant BACE-2 (extracellular domain, expressed in baculovirus and purified using standard methods) at 0.1 to 10 nM concentrations is incubated with the test compound at various concentrations for 1 hour at room temperature in 10 to 100 mM acetate buffer, pH 4.5, containing 0.1% CHAPS. Synthetic fluorescence-quenched peptide substrate, derived from the sequence of APP and containing a suitable fluorophore-quencher pair, is added to a final concentration of 1 to 5 μM, and the increase in fluorescence is recorded at a suitable excitation/emission wavelength in a microplate spectro-fluorimeter for 5 to 30 minutes in 1-minute intervals. $IC_{50}$ values are calculated from percentage of inhibition of BACE-2 activity as a function of the test compound concentration.

Test 3: Inhibition of Human Cathepsin D

Recombinant cathepsin D (expressed as procathepsin D in baculovirus, purified using standard methods and activated by incubation in sodium formate buffer pH 3.7) is incubated with the test compound at various concentrations for 1 hour at room temperature in sodium formate or sodium acetate buffer at a suitable pH within the range of pH 3.0 to 5.0. Synthetic peptide substrate Mca-Gly-Lys-Pro-Ile-Leu-Phe-Phe-Arg-Leu-Lys(DNP)-D-Arg-NH$_2$ is added to a final concentration of 1 to 5 μM, and the increase in fluorescence is recorded at excitation of 325 nm and emission at 400 nm in a microplate spectro-fluorimeter for 5 to 30 minutes in 1-minute intervals. $IC_{50}$ values are calculated from the percentage of inhibition of cathepsin D-activity as a function of the test compound concentration.

Test 4: Inhibition of Cellular Release of Amyloid Peptide 1-40

Chinese hamster ovary cells are transfected with the human gene for amyloid precursor protein. The cells are plated at a density of 8000 cells/well into 96-well microtiter plates and cultivated for 24 hours in DMEM cell culture medium containing 10% FCS. The test compound is added to the cells at various concentrations, and the cells are cultivated for 24 hours in the presence of the test compound. The supernatants are collected, and the concentration of amyloid peptide 1-40 is determined using state of the art immunoassay techniques, for example sandwich ELISA, homogenous time-resolved fluorescence (HTRF) immunoassay, or electro-chemiluminescence immunoassay. The potency of the compound is calculated from the percentage of inhibition of amyloid peptide release as a function of the test compound concentration.

Amorphous and crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide were tested in the above-described Test 1 and Test 4.

The compound of the Examples shows the following mean $IC_{50}$ values in Test 1:

TABLE 1

| Example | BABE-1 $IC_{50}$ [μM] | Number of Times Tested |
|---|---|---|
| 1 Amorphous | 0.0065 | 12 |
| 1 Crystalline | 0.0039 | 20 |

The compound of the Examples shows the following mean $IC_{50}$ values in Test 4:

TABLE 2

| Example | Amyloid-β1-40 release $IC_{50}$ [μM] | Number of Times Tested |
|---|---|---|
| 1 Amorphous | 0.0026 | 16 |
| 1 Crystalline | 0.0020 | 19 |

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the invention refers to an amount of the compound of the invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the invention that, when administered to a subject, is effective to (1) at least partially alleviating, inhibiting, preventing and/or ameliorating a condition, or a disorder or a disease (i) mediated by BACE-1 or (ii) associated with BACE-1 activity, or (iii) characterized by activity (normal or abnormal) of BACE-1; or (2) reducing or inhibiting the activity of BACE-1. In another non-limiting embodiment, the term "a therapeutically effective amount" refers to the amount of the compound of the invention that, when administered to a cell, or a tissue, or a non-cellular biological material, or a medium, is effective to at least partially reduce or inhibit the activity of BACE-1. The meaning of the term "a therapeutically effective amount" as illustrated in the above embodiments for BACE-1 also applies by the same means to any other relevant proteins/peptides/enzymes, such as BACE-2, or cathepsin D.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both.

As used herein, the term "prevention" of any particular disease or disorder refers to the administration of a compound of the invention to a subject before any symptoms of that disease or disorder are apparent.

As used herein, a subject is "in need of" a treatment if such subject would benefit biologically, medically or in quality of life from such treatment.

As used herein, the term an "agent" of the invention is used interchangeably with the term a "compound" of the invention and has no difference in meaning therefrom.

As used herein, the term "a," "an," "the" and similar terms used in the context of the invention (especially in the context of the claims) are to be construed to cover both the singular and plural unless otherwise indicated herein or clearly contradicted by the context. The use of any and all examples, or exemplary language (e.g. "such as") provided herein is intended merely to better illuminate the invention and does not pose a limitation on the scope of the invention otherwise claimed.

Due to its inhibiting properties towards proteases, the agent of the invention may be useful, e.g., in the treatment or prevention of a variety of disabilitating psychiatric, psychotic, neurological or vascular states, e.g. of a condition, disease or disorder of the vascular system or of the nervous system, in which beta-amyloid generation or aggregation plays a role, or, based on the inhibition of BACE-2 (beta-site APP-cleaving enzyme 2) or cathepsin D, which are close homologues of the pepsin-type aspartyl proteases and beta-secretase, and the correlation of the BACE-2 or cathepsin D expression with a more tumorigenic or metastatic potential of tumor cells, as anti-cancer medicaments, e.g. in the suppression of the metastasis process associated with tumor cells. The said condition, disease or disorder of the vascular system or of the nervous system is exemplified by, and includes, without limitation, an anxiety disorder, such as panic disorder with or without agoraphobia, agoraphobia without history of panic disorder, an animal or other specific phobia, including a social phobia, social anxiety disorder, anxiety, obsessive-compulsive disorder, a stress disorder, including post-traumatic or acute stress disorder, or a generalized or substance-induced anxiety disorder; a neurosis; seizures; epilepsy, especially partial seizures, simple, complex or partial seizures evolving to secondarily generalized seizures or generalized seizures [absence (typical or atypical), myoclonic, clonic, tonic, tonic-clonic or atonic seizures]; convulsions; migraine; an affective disorder, including a depressive or bipolar disorder, e.g. single-episode or recurrent major depressive disorder, major depression, a dysthymic disorder, dysthymia, depressive disorder NOS, bipolar I or bipolar II manic disorder or cyclothymic disorder; a psychotic disorder, including schizophrenia or depression; neurodegeneration, e.g. neurodegeneration arising from cerebral ischemia; an acute, traumatic or chronic degenerative process of the nervous system, such as Parkinson's disease, Down's syndrome, dementia, e.g. senile dementia, dementia with Lewy bodies or a fronto-temporal dementia, a cognitive disorder, cognitive impairment, e.g. mild cognitive impairment, memory impairment, an amyloid neuropathy, a peripheral neuropathy, Alzheimer's disease, Gerstmann-Straeussler-Scheinker syndrome, Niemann-Pick disease, e.g. Niemann-Pick type C disease, brain inflammation, a brain, spinal cord or nerve injury, e.g. traumatic brain injury (TBI), a nerve trauma or a brain trauma, vascular amyloidosis, cerebral haemorrhage with amyloidosis, Huntington's chorea, amyotrophic lateral sclerosis, multiple sclerosis or fragile X syndrome; scrapie; cerebral amyloid angiopathy; an encephalopathy, e.g. transmissible spongiform encephalopathy; stroke; an attention disorder, e.g. attention deficit hyperactivity disorder; Tourette's syndrome; a speech disorder, including stuttering; a disorder of the circadian rhythm, e.g. in subjects suffering from the effects of jet lag or shift work; pain; nociception; itch; emesis, including acute, delayed or anticipatory emesis, such as emesis induced by chemotherapy or radiation, motion sickness, or post-operative nausea or vomiting; an eating disorder, including anorexia nervosa or bulimia nervosa; premenstrual syndrome; a muscle spasm or spasticity, e.g. in paraplegic patients; a hearing disorder, e.g. tinnitus or age-related hearing impairment; urinary incontinence; glaucoma; inclusion-body myositis; or a substance-related disorder, including substance abuse or dependency, including a substance, such as alcohol, withdrawal disorder. An agent of the invention may also be useful in enhancing cognition, e.g. in a subject suffering from a dementing condition, such as Alzheimer's disease; as premedication prior to anaesthesia or a minor medical intervention, such as endoscopy, including gastric endoscopy; or as ligands, e.g. radioligands or positron emission tomography (PET) ligands.

For the above-mentioned indications, the appropriate dosage will vary depending on, e.g., the compound employed as active pharmaceutical ingredient, the host, the mode of administration, the nature and severity of the condition, disease or disorder or the effect desired. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 0.5 to about 2000, preferably from about 2 to about 200, mg of an agent of the invention conveniently administered, for example, in divided doses up to four times a day or in sustained release form.

An agent of the invention may be administered by any conventional route, in particular enterally, preferably orally, e.g. in the form of a tablet or capsule, or parenterally, e.g. in the form of an injectable solution or suspension.

In a further aspect, the invention relates to a pharmaceutical composition comprising the agent of the invention as active pharmaceutical ingredient in association with at least one pharmaceutically acceptable carrier or diluent and optionally in association with other auxiliary substances, such as inhibitors of cytochrome P450 enzymes, agents preventing the degradation of active pharmaceutical ingredients by cytochrome P450, agents improving or enhancing the pharmacokinetics of active pharmaceutical ingredients, agents improving or enhancing the bioavailability of active pharmaceutical ingredients, and so on, e.g. grapefruit juice, ketoconazole or, preferably, ritonavir. Such a composition may be manufactured in conventional manner, e.g. by mixing its components. Unit dosage forms contain, e.g., from about 0.1 to about 1000, preferably from about 1 to about 500, mg of an agent of the invention.

In addition, the pharmaceutical compositions of the invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with
- a) diluents, e.g., lactose, dextrose, sucrose, mannitol, sorbitol, cellulose and/or glycine;
- b) lubricants, e.g., silica, talcum, stearic acid, its magnesium or calcium salt and/or polyethyleneglycol; for tablets also
- c) binders, e.g., magnesium aluminum silicate, starch paste, gelatin, tragacanth, methylcellulose, sodium carboxymethylcellulose and/or polyvinylpyrrolidone; if desired
- d) disintegrants, e.g., starches, agar, alginic acid or its sodium salt, or effervescent mixtures; and/or
- e) absorbents, colorants, flavors and sweeteners.

Tablets may be either film coated or enteric coated according to methods known in the art.

Suitable compositions for oral administration include an effective amount of the compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of the compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The invention further provides anhydrous pharmaceutical compositions and dosage forms comprising the compound of the invention as an active ingredient, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the invention as an active ingredient will decompose. Such agents, which are referred to herein as "stabilizers," include, but are not limited to, antioxidants such as ascorbic acid, pH buffers, or salt buffers, etc.

In accordance with the foregoing, in a further aspect, the invention relates to the agent of the invention for use as a medicament, for example for the treatment or prevention of a neurological or vascular condition, disease or disorder, in which beta-amyloid generation or aggregation plays a role, or for the suppression of the metastasis process associated with tumor cells. In a further embodiment, the invention relates to the agent of the invention for use in the treatment or prevention of a disease or disorder mediated by BACE-1, BACE-2 or cathepsin D activity. In one embodiment, the invention relates to the agent of the invention for use in the treatment or prevention of Alzheimer's Disease or mild cognitive impairment.

In a further aspect, the invention relates to the use of the agent of the invention as an active pharmaceutical ingredient in a medicament, for example for the treatment or prevention of a neurological or vascular condition, disease or disorder, in which beta-amyloid generation or aggregation plays a role, or for the suppression of the metastasis process associated with tumor cells. In a further embodiment, the invention relates to the use of the agent of the invention as an active pharmaceutical ingredient in a medicament for the treatment or prevention of a disease or disorder mediated by BACE-1, BACE-2 or cathepsin D activity. In one embodiment, the invention relates to the use of the agent of the invention as an active pharmaceutical ingredient in a medicament for the treatment or prevention of Alzheimer's Disease or mild cognitive impairment.

In a further aspect, the invention relates to the use of the agent of the invention for the manufacture of a medicament for the treatment or prevention of a neurological or vascular condition, disease or disorder, in which beta-amyloid generation or aggregation plays a role, or for the suppression of the metastasis process associated with tumor cells. In a further embodiment, the invention relates to the use of the agent of the invention for the manufacture of a medicament for the treatment or prevention of a disease or disorder mediated by BACE-1, BACE-2 or cathepsin D activity. In one embodiment, the invention relates to the use of the agent of the invention for the manufacture of a medicament for the treatment or prevention of Alzheimer's Disease or mild cognitive impairment.

In a further aspect, the invention relates to a method for the treatment or prevention of a neurological or vascular condition, disease or disorder, in which beta-amyloid generation or aggregation plays a role, or for the suppression of the metastasis process associated with tumor cells, in a subject in need of such treatment, prevention or suppression, which method comprises administering to such subject an effective amount of the agent of the invention. In one embodiment, the invention relates to a method of modulating BACE-1, BACE-2 or cathepsin D activity in a subject, wherein the method comprises administering to the subject a therapeutically effective amount of the agent of the invention. In another embodiment, the invention relates to a method for the treatment or prevention of a disease mediated by BACE-1, BACE-2 or cathepsin D activity, in a subject in need of such treatment or prevention, which method comprises administering to such subject an effective amount of the agent of the invention. In yet another embodiment, the invention relates to a method for the treatment or prevention of Alzheimer's Disease or mild cognitive impairment, in a subject in need of such treatment or prevention, which method comprises administering to such subject an effective amount of the agent of the invention.

The agent of the invention can be administered as sole active pharmaceutical ingredient or as a combination with at least one other active pharmaceutical ingredient effective, e.g., in the treatment or prevention of a neurological or vascular condition, disease or disorder, in which beta-amyloid generation or aggregation plays a role, or in the suppression of the metastasis process associated with tumor cells. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e.g. a pack or dispenser-device adapted for the concomitant or separate administration of the at least two active components, in which these active components are separately arranged. In a further aspect, the invention relates to such pharmaceutical combinations.

In a further aspect, the invention therefore relates to a pharmaceutical combination comprising a therapeutically effective amount of the agent of the invention and a second drug substance, for simultaneous or sequential administration.

In one embodiment, the invention provides a product comprising the agent of the invention and at least one other therapeutic agent as a combined preparation for simultaneous, separate or sequential use in therapy. In one embodiment, the therapy is the treatment of a disease or condition mediated by BACE-1, BACE-2 or cathepsin D activity.

In one embodiment, the invention provides a pharmaceutical composition comprising the agent of the invention and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains the agent of the invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the agent of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides the agent of the invention for use in the treatment of a disease or condition mediated by BACE-1, BACE-2 or cathepsin D activity, wherein the medicament is prepared for administration with another therapeutic agent. The invention also provides the use of another therapeutic agent for treating a disease or condition mediated by BACE-1, BACE-2 or cathepsin D activity, wherein the medicament is administered with the agent of the invention.

The invention also provides the agent of the invention for use in a method of treating a disease or condition mediated by BACE-1, BACE-2 or cathepsin D activity, wherein the agent of the invention is prepared for administration with another therapeutic agent. The invention also provides another therapeutic agent for use in a method of treating a disease or condition mediated by BACE-1, BACE-2 or cathepsin D activity, wherein the other therapeutic agent is prepared for administration with the agent of the invention. The invention also provides the agent of the invention for use in a method of treating a disease or condition mediated by BACE-1, BACE-2 or cathepsin D activity, wherein the agent of the invention is administered with another therapeutic agent. The invention also provides another therapeutic agent for use in a method of treating a disease or condition mediated by BACE-1, BACE-2 or cathepsin D activity, wherein the other therapeutic agent is administered with the agent of the invention.

The invention also provides the use of the agent of the invention for treating a disease or condition mediated by BACE-1, BACE-2 or cathepsin D activity, wherein the patient has previously (e.g. within 24 hours) been treated with another therapeutic agent. The invention also provides the use of another therapeutic agent for treating a disease or condition mediated by BACE-1, BACE-2 or cathepsin D activity, wherein the patient has previously (e.g. within 24 hours) been treated with the agent of the invention.

In one embodiment, the invention relates to the compound of the invention in combination with another therapeutic agent wherein the other therapeutic agent is selected from:
(a) acetylcholinesterase inhibitors, such as donepezil (Aricept™), rivastigmine (Exelon™) and galantamine (Razadyne™);
(b) glutamate antagonists, such as memantine (Namenda™);
(c) antidepressant medications for low mood and irritability, such as citalopram (Celexa™) fluoxetine (Prozac™), paroxeine (Paxil™), sertraline (Zoloft™) and trazodone (Desyrel™);
(d) anxiolytics for anxiety, restlessness, verbally disruptive behavior and resistance, such as lorazepam (Ativan™) and oxazepam (Serax™);
(e) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(f) mood stabilizers, such as carbamazepine (Tegretol™) and divalproex (Depakote™);
(g) nicotinic apha-7 agonists;
(h) mGluR5 antagonists;
(i) H3 agonists; and
(j) amyloid therapy vaccines.

In another embodiment, the invention provides a pharmaceutical composition comprising:
i) a compound of the invention, or a pharmaceutically acceptable salt thereof;
ii) at least one therapeutic agent selected from:
    a) acetylcholinesterase inhibitors,
    b) glutamate antagonists,
    c) antidepressant medications,
    d) anxiolytics,
    e) antipsychotic medications,
    f) mood stabilizers,
    g) nicotinic apha-7 agonists,
    h) mGluR5 antagonists,
    i) H3 agonists, and
    j) amyloid therapy vaccines; and
iii) one or more pharmaceutically acceptable carriers or diluents.

The following Examples illustrate the invention.

EXAMPLES

List of Abbreviations

| | |
|---|---|
| DMAP | 4-dimethylaminopyridine |
| DMF | dimethylformamide |
| DMSO | dimethylsulfoxide |
| EDC | 1-(3-dimethylaminopropyl)-3-ethylcarbodiimide hydrochloride |
| EtOAc | ethyl acetate |
| h | hour(s) |
| i-PrOH | isopropanol |
| nBuLi | n-butyllithium |
| NEt$_3$ | triethylamine |
| Pd$_2$(dba)$_3$ | tris(dibenzylideneacetone)dipalladium(0) |
| TBME | tert-butyl-methyl-ether |
| tBu$_3$P | tri-tert-butyl phosphine |
| TFA | trifluoroacetic acid |
| THF | tetrahydrofuran |
| TLC | thin layer chromatography |

General chromatography information

HPLC method H1 (Rt$_{H1}$):

| | |
|---|---|
| HPLC-column dimensions: | 3.0 × 30 mm |
| HPLC-column type: | Zorbax SB-C18, 1.8 μm |
| HPLC-eluent: | A) water + 0.05 Vol.-% TFA; B) ACN + 0.05 Vol.-% TFA |
| HPLC-gradient: | 30-100% B in 3.25 min, flow = 0.7 ml/min |

LCMS method H3 (Rt$_{H3}$):

| | |
|---|---|
| HPLC-column dimensions: | 3.0 × 30 mm |
| HPLC-column type: | Zorbax SB-C18, 1.8 μm |
| HPLC-eluent: | A) water + 0.05 Vol.-% TFA, B) ACN + 0.05 Vol.-% TFA |
| HPLC-gradient: | 10-100% B in 3.25 min, flow = 0.7 ml/min |

UPLC method H5 (Rt$_{H5}$):

| | |
|---|---|
| HPLC-column dimensions: | 2.1 × 50 mm |
| HPLC-column type: | Acquity UPLC HSS T3 C18, 1.7 μm |
| HPLC-eluent: | A) water + 0.1 Vol.-% TFA, B) ACN + 0.1 Vol.-% TFA |
| HPLC-gradient: | 5-100% B in 1.5 min, flow = 1.0 ml/min |

Example 1

Preparation of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form a) 2-(5-Bromo-2-fluoro-phenyl)-propan-2-ol

To a solution of diisopropyl amine (57.3 ml, 402 mmol) in THF (500 ml) was added under argon a 1.6 M solution of nBuLi in hexane (260 ml, 416 mmol) below −50° C. After stirring for 30 min at −75° C., 4-bromo-1-fluoro benzene (31.1 ml, 277 mmol) was added while keeping the temperature below −70° C. After stirring for 2 h at −75° C., acetone (41.2 ml, 554 mmol) was added below −65° C. and the reaction mixture was stirred for 1 h at −75° C., warmed up to −50° C. and poured onto 10% aqueous $NH_4Cl$ solution. The mixture was extracted with TBME, organic phases were washed with aqueous $KHSO_4$ solution, saturated $NaHCO_3$ solution and brine, dried over $MgSO_4$, filtered and concentrated. The crude product was crystallized from hexane to provide the title compound as white crystals: TLC (hexane-EtOAc 3:1): Rf=0.45; UPLC $Rt_{H5}$=1.045 min; $^1$H NMR (360 MHz, $CDCl_3$): δ 7.74 (dd, 1H), 7.36 (m, 1H), 6.93 (dd, 1H), 2.04 (d, 1H), 1.63 (s, 6H).

b) 4-Bromo-1-fluoro-2-isopropenyl-benzene

To a solution of 2-(5-bromo-2-fluoro-phenyl)-propan-2-ol (119.7 g, 498 mmol) in $CH_2Cl_2$ (50 ml) was added hydrochinone (2.74 g, 24.9 mmol) and 250 ml 85% $H_3PO_4$. The resulting reaction mixture was stirred for 3.5 h at 50° C. The mixture was poured onto ice-water and extracted with $CH_2Cl_2$. The organic phases were washed with 2N aqueous NaOH and water, dried over $MgSO_4$, filtered and concentrated. The crude product was dissolved in hexane and filtered through a plough of silica gel to obtain after concentration at 600 mbar the title compound as a colorless oil: TLC (hexane): Rf=0.52; UPLC $Rt_{H5}$=1.416 min; $^1$H NMR (360 MHz, $CDCl_3$): δ 7.43 (dd, 1H), 7.37 (m, 1H), 6.94 (dd, 1H), 5.27 (d, 2H), 2.13 (s, 3H).

c) (S)-2-(5-Bromo-2-fluoro-phenyl)-propane-1,2-diol

To a suspension of $K_3Fe(CN)_6$ (186 g, 561 mmol), $K_2CO_3$ (78 g, 561 mmol), $(DHQ)_2$-PHAL (1.311 g, 1.674 mmol) and $K_2OsO_2(OH)_4$ (0.378 g, 1 mmol) in t-BuOH—$H_2O$ 1:1 (1600 ml) was added 4-bromo-1-fluoro-2-isopropenyl-benzene (36 g, 167 mmol) at 0° C. and the reaction mixture was stirred for 14 h at 0° C. After careful addition of $Na_2S_2O_5$ (100 g) at 0-5° C. the reaction mixture was stirred for 1 h before extraction with EtOAc. Combined extracts were washed with 5% $NaS_3O_3$ solution and brine, dried over $MgSO_4$, filtered and concentrated to give the title compound as a white solid: TLC (hexane-EtOAc 1:1): Rf=0.46; UPLC $Rt_{H5}$=0.767 min; ESIMS: 266, 268 [(M+$NH_4$)$^+$]; $^1$H NMR (360 MHz, $CDCl_3$): δ 7.71 (dd, 1H), 7.27 (m, 1H), 6.83 (dd, 1H), 3.85 (d, 1H), 3.62 (d, 1H), 2.94 (s, 3H), 2.01 (s, 1H), 1.43 (s, 3H).

d) (S)-2-(5-Bromo-2-fluoro-phenyl)-2-methyl-oxirane

To a solution of (S)-2-(5-bromo-2-fluoro-phenyl)-propane-1,2-diol (37.35 g, 150 mmol) in $CH_2Cl_2$ (400 ml) was added under argon $NEt_3$ (41.8 ml, 300 mmol) and dropwise mesyl chloride (12.8 ml, 165 mmol) at 0-5° C. After stirring for 0.5 h at 0-5° C. the reaction mixture was added to cold 1N HCl and extracted with $CH_2Cl_2$. Combined extracts were washed with 1N HCl, $H_2O$ and saturated $NaHCO_3$ solution, dried over $MgSO_4$, filtered and concentrated. The crude mesylate was dissolved in TBME (500 ml) and 200 ml 2N aqueous NaOH and after stirring for 2 h at 25° C. the mixture was extracted with TBME. Combined extracts were washed with $NaH_2PO_4$ solution and brine, dried over $MgSO_4$, filtered and concentrated to provide the (S)-enantiomer as a colorless oil: 78% ee (Chiralpak AS-H 1218, hexane-EtOH 97:3, 0.4 mL/min); TLC (hexane-EtOAc 3:1): Rf=0.69; UPLC $Rt_{H5}$=1.186 min; $^1$H NMR (360 MHz, $CDCl_3$): δ 7.46 (dd, 1H), 7.30 (m, 1H), 6.83 (dd, 1H), 2.88 (d, 1H), 2.72 (d, 1H), 1.59 (s, 3H).

e) (S)-1-Azido-2-(5-bromo-2-fluoro-phenyl)-propan-2-ol

To a solution of (S)-2-(5-bromo-2-fluoro-phenyl)-2-methyl-oxirane (51.85 g, 224 mmol) in EtOH (800 ml) was added $NaN_3$ (36.8 g, 531 mmol), $NH_4Cl$ (60.6 g, 1122 mmol) and 18-crown-6 (59.8 g, 224 mmol) and the reaction mixture was heated at reflux for 6 h. The reaction mixture was filtered and concentrated to half of its volume. The residual oil was extracted with EtOAc. Combined extracts were washed with saturated $NaHCO_3$ solution and brine, dried over $MgSO_4$, filtered and concentrated to provide the title compound as a light yellow oil: TLC (hexane-EtOAc 1:1): Rf=0.70; UPLC $Rt_{H3}$=1.115 min; $^1$H NMR (360 MHz, $CDCl_3$): δ 7.72 (dd, 1H), 7.32 (m, 1H), 6.85 (dd, 1H), 3.73 (d, 1H), 3.51 (d, 1H), 2.44 (s, 1H), 1.50 (s, 3H).

f) (S)-1-Amino-2-(5-bromo-2-fluoro-phenyl)-propan-2-ol

To a suspension of $LiAlH_4$ (4.65 g, 122 mmol) in THF (250 ml) was added under argon at 0-5° C. a solution of (S)-1-azido-2-(5-bromo-2-fluoro-phenyl)-propan-2-ol (33.4 g, 122 mmol) dissolved in THF (150 ml) over a period of 30 min. After stirring for 1 h at 0-5° C., the reaction was quenched by careful addition of water (4.7 ml), 4 N NaOH (4.7 ml) and water (14.1 ml) and stirred again for 3 h at 25° C. The white suspension was dried with $MgSO_4$, filtered and concentrated. The solidified product was re-crystallized from TBME-hexane to provide the title compound as beige crystals: 98% ee (Chiralpak AD-H hexane-EtOH 75-25+0.05% $NEt_3$); TLC ($CH_2Cl_2$-MeOH 10:1) Rf=0.10; UPLC $Rt_{H5}$=0.558 min; ESIMS: 248, 250 [(M+H)$^+$]; $^1$H NMR (360 MHz, $CDCl_3$): δ 7.76 (dd, 1H), 7.25 (m, 1H), 6.82 (dd, 1H), 4.16 (br s, 1H), 3.19 (d, 1H), 2.72 (d, 1H), 1.44 (s, 3H), 0.95 (br s, 2H).

g) N—[(S)-2-(5-Bromo-2-fluoro-phenyl)-2-hydroxypropyl]-2-nitro-benzenesulfonamide To a solution of (S)-1-amino-2-(5-bromo-2-fluoro-phenyl)-propan-2-ol (34.7 g, 140 mmol) in THF (400 ml) was added 2-nitro-benzenesulfonyl chloride (34.9 g, 154 mmol) at 0-5° C. and afterwards 1N aqueous NaOH over a period of 0.5 h. The reaction mixture was stirred for 2 h at 20° C. The reaction mixture was diluted with TBME and washed with water and NaH$_2$PO$_4$ solution and brine, dried over MgSO$_4$, filtered and concentrated to provide the title compound after crystallization from TBME-hexane as beige crystals: TLC (toluene-EtOAc 3:1): Rf=0.51; UPLC Rt$_{H5}$=1.118 min; ESIMS: 450, 452 [(M+NH$_a$)$^+$]; $^1$H NMR (360 MHz, CDCl$_3$): δ 7.98 (m, 1H), 7.81 (m, 1H), 7.65 (m, 2H), 7.59 (dd, 1H), 7.24 (m, 1H), 6.79 (dd, 1H), 5.60 (t, 1H), 4.16 (br s, 1H), 3.55 (dd, 1H), 3.44 (dd, 1H), 2.51 (s, 1H), 1.51 (s, 3H).

h) (R)-2-(5-Bromo-2-fluoro-phenyl)-2-methyl-1-(2-nitro-benzenesulfonyl)-aziridine To a solution of N—[(S)-2-(5-bromo-2-fluoro-phenyl)-2-hydroxy-propyl]-2-nitro-benzenesulfon-amide (20.8 g, 48 mmol) in CH$_2$Cl$_2$ (400 ml) was added PPh$_3$ (19.2 g, 72.4 mmol) at 0-5° C. and diethyl azodicarboxylate (11.6 ml, 72.4 mmol). The reaction mixture was stirred for 24 h at 25° C. and concentrated. The title compound was obtained after chromatographic purification over silica gel (hexane-EtOAc 20:1 to 2:1) as yellow crystals: TLC (toluene-EtOAc 3:1): Rf=0.69; UPLC Rt$_{H5}$=1.308 min; $^1$H NMR (360 MHz, CDCl$_3$): δ 8.31 (m, 1H), 7.28 (m, 3H), 7.60 (dd, 1H), 7.42 (m, 1H), 6.91 (dd, 1H), 3.24 (s, 1H), 2.81 (s, 1H), 2.06 (s, 3H).

i) (R)-2-[(R)-2-(5-Bromo-2-fluoro-phenyl)-2-(2-nitro-benzenesulfonylamino)-propoxy]-3,3,3-trifluoro-2-methyl-propionic acid ethyl ester To a suspension of NaH (2.53 g 60% in mineral oil, 63 mmol) in DMF (160 ml) was added drop-wise under argon (R)-3,3,3-trifluoro-2-hydroxy-2-methyl-propionic acid ethyl ester (11.99 g, 63 mmol) and after stirring for 0.5 h at 20° C. (R)-2-(5-bromo-2-fluoro-phenyl)-2-methyl-1-(2-nitro-benzenesulfonyl)-aziridine (21.85 g, 52.6 mmol). The reaction was kept at 25° C. for 16 h. The mixture was added to cold aqueous 2N HCl and the product extracted with TBME. Combined organic layers were washed with saturated NaHCO$_3$ solution and brine, dried over MgSO$_4$, filtered and concentrated. The residual solid was re-crystallized from TBME-hexane to provide the title compound as yellow crystals: TLC (hexane-EtOAc 1:1): Rf=0.59; UPLC Rt$_{H5}$=1.444 min; ESIMS: 618, 620 [(M+NH$_4$)$^+$]; $^1$H NMR (360 MHz, CDCl$_3$): δ 7.83 (dd, 1H), 7.61 (m, 3H), 7.48 (dd, 1H), 7.27 (m, 1H), 6.73 (s, 1H), 6.60 (dd, 1H), 4.33 (m, 2H), 3.84 (s, 2H), 1.84 (s, 3H), 1.57 (s, 3H), 1.33 (t, 3H).

j) (R)-2-[(R)-2-(5-Bromo-2-fluoro-pheyl)-2-(2-nitro-benzenesulfonylamino)-propoxy]-3,3,3-trifluoro-2-methyl-propionamide A solution of (R)-2-[(R)-2-(5-bromo-2-fluoro-phenyl)-2-(2-nitro-benzenesulfonylamino)-propoxy]-3,3,3-trifluoro-2-methyl-propionic acid ethyl ester (26.6 g, 44.2 mmol) in 7N NH$_3$ in MeOH (75 ml) was stirred for 16 h at 50° C. The solvent was removed under reduced pressure and the residual solid re-crystallized from Et$_2$O to give the title compound as yellow crystals: TLC (hexane-EtOAc 1:1): Rf=0.35; UPLC Rt$_{H5}$=1.184 min; ESIMS: 589, 591 [(M+NH$_4$)$^+$]; $^1$H NMR (360 MHz, CDCl$_3$): δ 7.85 (d, 1H), 7.64 (m, 3H), 7.44 (d, 1H), 7.41 (dd, 1H), 7.26 (m, 1H), 6.68 (br s, 1H), 6.57 (dd, 1H), 6.19 (s, 1H), 5.54 (br s, 1H), 4.24 (d, 1H), 3.93 (d, 1H), 1.79 (s, 3H), 1.67 (s, 3H).

k) N—[(R)-1-(5-Bromo-2-fluoro-phenyl)-2-((R)-1-cyano-2,2,2-trifluoro-1-methyl-ethoxy)-1-methyl-ethyl]-2-nitro-benzenesulfonamide To a solution of (R)-2-[(R)-2-(5-bromo-2-fluoro-pheyl)-2-(2-nitro-benzenesulfonylamino)-propoxy]-3,3,3-trifluoro-2-methyl-propionamide (20.83 g, 35.6 mmol) in CH$_2$Cl$_2$ (300 ml) was added under argon NEt$_3$ (12.5 ml, 89 mmol) and at 0-5° C. trifluoroacetic anhydride (6.15 ml, 42.7 mmol). After stirring for 4 h at 25° C. the reaction mixture was added to a cold NaHCO$_3$ solution and the product was extracted with CH$_2$Cl$_2$. Combined extracts were washed with cold 0.1N aqueous HCl, water and saturated NaHCO$_3$ solution, dried over MgSO$_4$, filtered and concentrated to provide the title compound as a yellow oil, which was used as such for the next step: TLC (hexane-EtOAc 1:1): Rf=0.73; UPLC Rt$_{H5}$=1.364 min; ESIMS: 571, 573 [(M+NH$_4$)$^+$]; $^1$H NMR (360 MHz, CDCl$_3$): δ 7.89 (d, 1H), 7.62 (ddd, 1H), 7.57 (ddd, 1H), 7.52 (m, 2H), 7.29 (m, 1H), 6.58 (dd, 1H), 6.19 (s, 1H), 4.17 (s, 2H), 1.81 (s, 3H), 1.72 (s, 3H).

l) (2R,5R)-5-(5-Bromo-2-fluoro-phenyl)-2,5-dimethyl-2-trifluoromethyl-5,6-dihydro-2H-[1,4]oxazin-3-ylamine To a solution of N—[(R)-1-(5-bromo-2-fluoro-phenyl)-2-((R)-1-cyano-2,2,2-trifluoro-1-methyl-ethoxy)-1-methyl-ethyl]-2-nitro-benzenesulfonamide (6.54 g, 11.8 mmol) and N-acetyl-cysteine (2.4 g, 26.0 mmol) in MeOH (80 ml) was added K$_2$CO$_3$ (3.62 g, 26.0 mmol) and the reaction mixture was heated at 80° C. for 16 h. After removal of the solvent the residue was dissolved in water and extracted with EtOAc. Combined extracts were washed with saturated NaHCO$_3$ solution and brine, dried over MgSO$_4$, filtered and concentrated to provide the title compound after chromatographic purification over silica gel (hexane-EtOAc 10:1 to 1:2 containing 0.03% NEt$_3$) as a yellow oil: TLC (hexane-EtOAc 1:1): Rf=0.58; UPLC Rt$_{H5}$=0.843 min; ESIMS: 369, 371 [(M+H)$^+$]; $^1$H NMR (360 MHz, CDCl$_3$): δ 7.66 (dd, 1H), 7.35 (m, 1H), 6.91 (dd, 1H), 3.97 (m, 2H), 1.53 (s, 3H), 1.49 (s, 3H).

m) (2R,5R)-5-(2-Fluoro-phenyl)-2,5-dimethyl-2-trifluoromethyl-5,6-dihydro-2H-[1,4]oxazin-3-ylamine A solution of (2R,5R)-5-(5-bromo-2-fluoro-phenyl)-2,5-dimethyl-2-trifluoromethyl-5,6-dihydro-2H-[1,4]oxazin-3-ylamine (1.66 g, 4.5 mmol) and sodium acetate (0.369 g, 4.5 mmol) in MeOH (50 ml) was hydrogenated over 10% Pd—C for 6 h at 50° C. The catalyst was filtered off over Celite and the filtrate was concentrated. The residue was dissolved in saturated NaHCO$_3$ solution and extracted with EtOAc. Combined extracts were washed with brine, dried over MgSO$_4$, filtered and concentrated to provide the title compound as a colorless oil: TLC (hexane-EtOAc 1:1): Rf=0.19; UPLC Rt$_{H5}$=0.777 min; ESIMS: 291 [(M+H)$^+$]; $^1$H NMR (360 MHz, CDCl$_3$): δ 7.41 (dt, 1H), 7.26 (m, 1H), 7.11 (t, 1H), 7.05 (dd, 1H), 4.11 (dd, 1H), 3.94 (dd, 1H), 1.54 (s, 3H), 1.49 (s, 3H).

n) (2R,5R)-5-(2-Fluoro-5-nitro-phenyl)-2,5-dimethyl-2-trifluoromethyl-5,6-dihydro-2H-[1,4]oxazin-3-ylamine To a solution of (2R,5R)-5-(2-fluoro-phenyl)-2,5-dimethyl-2-trifluoromethyl-5,6-dihydro-2H-[1,4]oxazin-3- ylamine (1.035 g, 3.57 mmol) in H₂SO₄ (6 ml) was added in portions KNO₃ (0.379 g, 3.74 mmol) under ice-water cooling. The reaction mixture was stirred for 2 h at 25° C., diluted with water and basified with K₂CO₃ under cooling. The product was extracted with EtOAc. Combined extracts were washed with saturated NaHCO₃ solution and brine, dried over MgSO₄, filtered and concentrated. Purification via chromatography on silica gel (hexane-EtOAc 4:1 to 1:1 containing 0.05% NEt₃) gave the title compound as a light yellow oil: TLC (hexane-EtOAc 1:1): Rf=0.50; UPLC Rt$_{H5}$=0.749 min; ESIMS: 336 [(M+H)⁺]; ¹H NMR (360 MHz, CDCl₃): δ 8.48 (dd, 1H), 8.14 (m, 1H), 7.15 (dd, 1H), 4.20 (br s, 2H), 4.04 (dd, 1H), 3.91 (dd, 1H), 1.54 (s, 3H), 1.49 (s, 3H).

o) [(2R,5R)-5-(2-Fluoro-5-nitro-phenyl)-2,5-dimethyl-2-trifluoromethyl-5,6-dihydro-2H-[1,4]oxazin-3-yl]-carbamic acid tert-butyl ester To a solution of (2R,5R)-5-(2-fluoro-5-nitro-phenyl)-2,5-dimethyl-2-trifluoromethyl-5,6-dihydro-2H-[1,4]oxazin-3-ylamine (1.14 g, 3.4 mmol) in ACN (20 ml) was added Boc₂O (0.891 g, 4.08 mmol) and NEt₃ (0.72 ml, 5.1 mmol) and the mixture was stirred for 16 h at 25° C. The reaction mixture was evaporated and the residual oil purified by chromatography on silica gel (hexane-EtOAc 20:1 to 7:3) to give the title compound after crystallization from Et₂O-hexane as beige crystals: TLC (hexane-EtOAc 3:1): Rf=0.37; UPLC Rt$_{H5}$=1.355 min; ESIMS: 436 [(M+H)⁺]; ¹H NMR (360 MHz, CDCl₃): δ 11.04 (br s, 1H), 8.24 (m, 2H), 7.30 (dd, 1H), 4.41 (dd, 1H), 4.11 (dd, 1H), 1.68 (s, 3H), 1.51 (s, 9H), 1.49 (s, 3H).

p) [(2R,5R)-5-(5-Amino-2-fluoro-phenyl)-2,5-dimethyl-2-trifluoromethyl-5,6-dihydro-2H-[1,4]oxazin-3-yl]-carbamic acid tert-butyl ester A solution of [(2R,5R)-5-(2-fluoro-5-nitro-phenyl)-2,5-dimethyl-2-trifluoromethyl-5,6-dihydro-2H-[1,4]oxazin-3-yl]-carbamic acid tert-butyl ester (0.98 g, 2.25 mmol) in isopropanol-THF 2:1 (24 ml) was hydrogenated over 5% Pd—C for 4 h at 50° C. The catalyst was filtered off over Celite and the filtrate was concentrated to provide the title compound after crystallization from TBME-hexane as beige crystals: TLC (hexane-EtOAc 1:1): Rf=0.42; UPLC Rt$_{H5}$=0.955 min; ESIMS: 406 [(M+H)⁺]; ¹H NMR (360 MHz, CDCl₃): δ 6.82 (dd, 1H), 6.52 (m, 2H), 4.30 (dd, 1H), 3.97 (dd, 1H), 3.06 (br s, 2H), 1.58 (s, 3H), 1.48 (s, 3H), 1.46 (s, 9H).

q) ((2R,5R)-5-{5-[(5-Cyano-3-methyl-pyridine-2-carbonyl)-amino]-2-fluoro-phenyl}-2,5-dimethyl-2-trifluoromethyl-5,6-dihydro-2H-[1,4]oxazin-3-yl)-carbamic acid tert-butyl ester To a solution of [(2R,5R)-5-(5-amino-2-fluoro-phenyl)-2,5-dimethyl-2-trifluoromethyl-5,6-dihydro-2H-[1,4]oxazin-3-yl]-carbamic acid tert-butyl ester (82 mg, 0.20 mmol) in DMF (2 ml) was added 5-cyano-3-methyl-pyridine-2-carboxylic acid (42 mg, 0.26 mmol), EDC.HCl (51 mg, 0.26 mmol), HOAt (31 mg, 0.22 mmol) and DIPEA (0.09 ml, 0.52 mmol) and the reaction mixture was kept at 25° C. for 16 h. The mixture was concentrated, the residue dissolved in EtOAc and washed with saturated NaHCO₃ solution and brine, dried over MgSO₄, filtered and purified by chromatography on silica gel (hexane-EtOAc 20:1 to 1:1) to provide the title compound as a light yellow foam: TLC (hexane-EtOAc 1:1): Rf=0.81; UPLC Rt$_{H5}$=1.437 min; ESIMS: 550 [(M+H)⁺]; ¹H NMR (360 MHz, CDCl₃): δ 10.96 (br s, 1H), 9.95 (br s, 1H), 8.63 (s, 2H), 7.88 (m, 1H), 7.71 (m, 1H), 7.54 (dd, 1H), 7.08 (dd, 1H), 4.34 (d, 1H), 4.02 (d, 1H), 2.77 (s, 3H), 1.63 (s, 3H), 1.47 (m, 12H).

r) Crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide To a solution of ((2R,5R)-5-{5-[(5-cyano-3-methyl-pyridine-2-carbonyl)-amino]-2-fluoro-phenyl}-2,5-dimethyl-2-trifluoromethyl-5,6-dihydro-2H-[1,4]oxazin-3-yl)-carbamic acid tert-butyl ester in CH₂Cl₂ (0.3 ml) was added TFA (0.6 ml) and the reaction mixture was kept at 25° C. for 2 h. The reaction was added to cold 10% aqueous K₂CO₃ solution and the product extracted with EtOAc. Combined organic layers were washed with brine, dried over MgSO₄, filtered and concentrated, then purified by CombiFlash (120 g silica gel, hexane —(CH₂Cl₂/MeOH 10:1) gradient 10:1 to 0:10) to provide 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide as a colorless foam. The amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide (2.6 g, 5.6 mmol) was dissolved in EtOH (15 mL) and after warming to 40° C. the solution was saturated with H₂O (ca. 6-7 mL). The crystallization was kept for 16 h at 25° C. before the crystals were collected, washed with cold EtOH—H₂O and dried under high vacuum for 16 h at 25° C. to provide the title compound as white needles: mp 101-102° C. UPLC Rt$_{H5}$=0.957 min; ESIMS: 450 [(M+H)⁺]; ¹H NMR (600 MHz, DMSO-d₆): δ 10.73 (br s, 1H), 8.98 (s, 1H), 8.41 (s, 1H), 7.80 (dd, 1H), 7.73 (m, 1H), 7.16 (dd, 1H), 6.08 (s, 2H), 3.92 (d, 1H), 3.80 (d, 1H), 2.54 (s, 3H), 1.47 (s, 3H), 1.42 (s, 3H).

Preparation of
5-cyano-3-methyl-pyridine-2-carboxylic acid

The 5-cyano-3-methyl-pyridine-2-carboxylic acid used in step q) above may be prepared as follows:

a) 5-Bromo-3-methyl-pyridine-2-carboxylic acid tert-butyl ester

To a solution of 10.20 g (47.2 mmol) 5-bromo-3-methyl-pyridine-2-carboxylic acid and 20.61 g (94 mmol) di-tert-butyldicarbonate in 100 ml THF were added 0.577 g DMAP. Evolution of CO₂ started immediately and the mixture was stirred for 2 h at RT. TBME and sat aq NaHCO₃ were added. The layers were separated and the organic layer washed with sat aq NaHCO₃ and brine, and dried with MgSO₄.H₂O. Chromatography on silica gel (hexanes/EtOAc 1-7%) provided the title compound as a yellow liquid. HPLC: Rt$_{H3}$=3.018 min; ESIMS [M+H]⁺=272, 274 (1 Br); ¹H-NMR (360 MHz, CDCl₃): δ 8.59 s, 1H), 7.77 (s, 1H), 2.52 (s, 3H), 1.65 (s, 9H).

b) 5-Bromo-3-methyl-pyridine-2-carboxylic acid tert-butyl ester

A mixture of 6.0 g (22.05 mmol) 5-bromo-3-methyl-pyridine-2-carboxylic acid tert-butyl ester, 1.813 g (15.43 mmol) Zn(CN)₂, 0.144 g Zn powder (2.205 mmol) and 0.571 g (0.551 mmol) Pd₂(dba)₃.CHCl₃ were suspended in 10 ml DMF under nitrogen atmosphere. tBu₃P (0.321 ml, 1.323 mmol) was added and the mixture was stirred for 5 h at 60° C.

After being cooled down the mixture was diluted with TBME, filtered over celite and washed with brine three times. The crude product was purified by column chromatography on silica gel (hexanes/EtOAc 5-15%) to give the title compound as an off white solid. TLC (hexanes/EtOAc 3:1): Rf=0.31; HPLC: $Rt_{H3}$=2.431 min; ESIMS [M+Na]$^+$=241; $^1$H-NMR (360 MHz, CDCl$_3$): δ 8.78 (s, 1H), 7.88 (s, 1H), 2.56 (s, 3H), 1.67 (s, 9H); Ft-IR: 2231 cm$^{-1}$ (CN).

c) 5-cyano-3-methyl-pyridine-2-carboxylic acid

To a solution of 8.50 g (38.9 mmol) 5-cyano-3-methyl-pyridine-2-carboxylic acid tert-butyl ester in 51 ml (389 mmol) 1,3-dimethoxybenzene were added 85 ml TFA and stirred for 6.5 h. The reaction mixture was diluted with toluene and evaporated. The residue was taken up in toluene and evaporated (2×). The product was crystallized from TBME/hexanes to give the title compound as a white powder. HPLC: $Rt_{H1}$=2.314 min; ESIMS [M+Na]$^+$=163; $^1$H-NMR (360 MHz, CDCl$_3$): δ 8.77 (s, 1H), 8.07 (s, 1H), 2.87 (s, 3H).

Example 2

First alternative procedure for the preparation of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form a) ((2R,5R)-5-{5-[(5-Cyano-3-methyl-pyridine-2-carbonyl)-amino]-2-fluoro-phenyl}-2,5-dimethyl-2-trifluoromethyl-5,6-dihydro-2H-[1,4]oxazin-3-yl)-carbamic acid tert-butyl ester To a solution of [(2R,5R)-5-(5-amino-2-fluoro-phenyl)-2,5-dimethyl-2-trifluoromethyl-5,6-dihydro-2H-[1,4]oxazin-3-yl]-carbamic acid tert-butyl ester (step p Example 1) (2.2 g, 5.43 mmol) in DMF (20 ml) was added at 0-5° C. 5-cyano-3-methyl-pyridine-2-carboxylic acid (0.968 g, 5.97 mmol), EDC (1.095 g, 7.05 mmol), HOAt (1.182 g, 8.68 mmol) and the reaction mixture was stirred at 25° C. for 16 h. The reaction mixture was added to cold saturated NaHCO$_3$ solution and the product was extracted with TBME. Combined TBME layers were washed with H$_2$O and brine, dried over MgSO$_4$, filtered and concentrated to obtain after crystallization from diisopropylether the title compound as colorless crystals: UPLC $Rt_{H5}$=1.472 min); ESIMS: 550; [(M+H)$^+$]; $^1$H NMR (400 MHz, CDCl$_3$): δ 11.11 (s, 1H), 10.11 (s, 1H), 8.79 (br s, 1H), 8.01 (s, 1H), 7.84 (m, 1H), 7.68 (dd, 1H), 7.21 (dd, 1H), 4.49 (d, 1H), 4.16 (d, 1H), 1.76 (s, 3H), 1.64 (s, 3H), 1.62 (s, 9H).

b) 5-Cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide To a solution of ((2R,5R)-5-{5-[(5-cyano-3-methyl-pyridine-2-carbonyl)-amino]-2-fluoro-phenyl}-2,5-dimethyl-2-trifluoromethyl-5,6-dihydro-2H-[1,4]oxazin-3-yl)-carbamic acid tert-butyl ester (2.27 g, 4.13 mmol) in CH$_2$Cl$_2$ (25 ml) was added TFA (41.3 mmol, 3.18 ml) and the reaction mixture was stirred at 25° C. for 2.5 h. The reaction mixture was added to 10% aqueous NaHCO$_3$ solution (pH>8) and the free base was extracted with EtOAc. Combined organic layers were washed with water and brine, dried over MgSO$_4$, filtered and concentrated. The crude product was re-crystallized twice by dissolving the material in EtOH (15 ml) at 50-60° C. and after saturation with H$_2$O (6-8 ml) the clear solution was allowed to cool to ambient temperature overnight to provide after filtration and drying the title compound in >99% purity as white crystals: UPLC $Rt_{H5}$=0.905 min; ESIMS: 450 [(M+H)$^+$]; $^1$H NMR (600 MHz, DMSO-d$_6$): 10.72 (s, 1H), 8.97 (s, 1H), 8.39 (s, 1H), 7.78 (d, 1H), 7.71 (m, 1H), 7.15 (t, 1H), 6.08 (br s, 2H), 3.91 (d, 1H), 3.78 (d, 1H), 2.52 (s, 3H), 1.46 (s, 3H), 1.41 (s, 3H).

Example 3

Second alternative procedure for the preparation of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form 5.954 mg of amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was dispersed in 400 uL of water at room temperature and cooled from 16° C. to 5° C. at 2.4° C./h, kept at 5° C. for 10 h and then heated to 40° C. at 5° C./min and cooled back to 5° C. at 2.4° C./h. The solids were isolated by centrifugation and dried at 37° C./50 mbar overnight.

Example 4

Third alternative procedure for the preparation of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form 4.9 mg of amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was slurried in 400 uL of ethanol/water 20/80 at room temperature for 24 h. The solids were then separated and dried at 37° C./50 mbar overnight.

Example 5

Fourth alternative procedure for the preparation of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form 4.9 mg of amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was slurried in 400 uL of acetone/water 20/80 at room temperature for 24 h. The solids were then separated and dried at 37° C./50 mbar overnight.

Example 6

Fifth alternative procedure for the preparation of 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide in crystalline form Amorphous 5-cyano-3-methyl-pyridine-2-carboxylic acid [3-((3R,6R)-5-amino-3,6-dimethyl-6-trifluoromethyl-3,6- dihydro-2H-[1,4]oxazin-3-yl)-4-fluoro-phenyl]-amide (395 g) was dissolved in i-PrOH (3 L) and heated to 60° C., at this point, water (3 L) was added at 60° C. The solution was cooled gradually to 0° C. to form a slurry. The solid was collected by filtration at 0-4° C. and the filter cake was washed with i-PrOH/water (1:1) (1 L), dried in a vacuum oven at 65° C. for 40 h to obtain crystalline material as a white solid: $^1$H NMR (400 MHz, DMSO-d6): δ 10.69 (s, 1H), 8.97 (s, 1H), 8.38 (s, 1H), 7.72~7.81 (m, 2H), 7.12~7.15 (q, 1H), 6.05 (br s, 2H), 3.78~3.93 (q, 2H), 2.54 (s, 3H), 1.47 (s, 3H), 1.42 (s, 3H).

Example 7

XRPD analysis of amorphous and crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide Crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was analysed by XRPD and the ten most characteristic peaks are shown in Table 3 (see also FIG. 1).

TABLE 3

| Degrees 2-Θ | d-spacing (Å) | Intensity (counts) | Relative Intensity % | |
|---|---|---|---|---|
| 8.335 | 10.59904 | 22.60 | 7.1 | Low |
| 9.032 | 9.78356 | 2013 | 6.3 | Low |
| 10.851 | 8.14682 | 6590 | 20.7 | Medium |
| 12.919 | 6.84703 | 7660 | 24.1 | Medium |
| 13.859 | 6.38459 | 31816 | 100 | High |
| 15.403 | 5.74799 | 15281 | 48.0 | Medium |
| 16.211 | 5.46313 | 6577 | 20.7 | Medium |
| 17.129 | 5.17238 | 8543 | 26.9 | Medium |
| 18.158 | 4.88155 | 5135 | 16.1 | Medium |
| 24.514 | 3.62838 | 10501 | 33 | Medium |

X-ray powder diffraction (XRPD) analysis was performed using a Brucker D8 Advance x-ray diffractometer. Measurements were taken at about 30 kV and 40 mA under the following conditions:

| | |
|---|---|
| Scan rate (continuous scan): | 0.3 s/step (equals 107.1 s step time) |
| Step size: | 0.017° (2Theta) |
| Soller slit | 2.5° |
| Slits (from left to right): | V12 (variable), 6 mm antiscatter slit |

The X-ray diffraction pattern was recorded between 2° and 40° (2 theta) with CuK$_\alpha$ radiation for identification of the whole pattern.

Example 8

DSC analysis of crystalline and amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide Crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was analysed by differential scanning calorimetry (DSC) using a Q1000 DSC from TA instruments and found to have an onset of melting at about 93.6° C., see FIG. 2.

Figure 3:
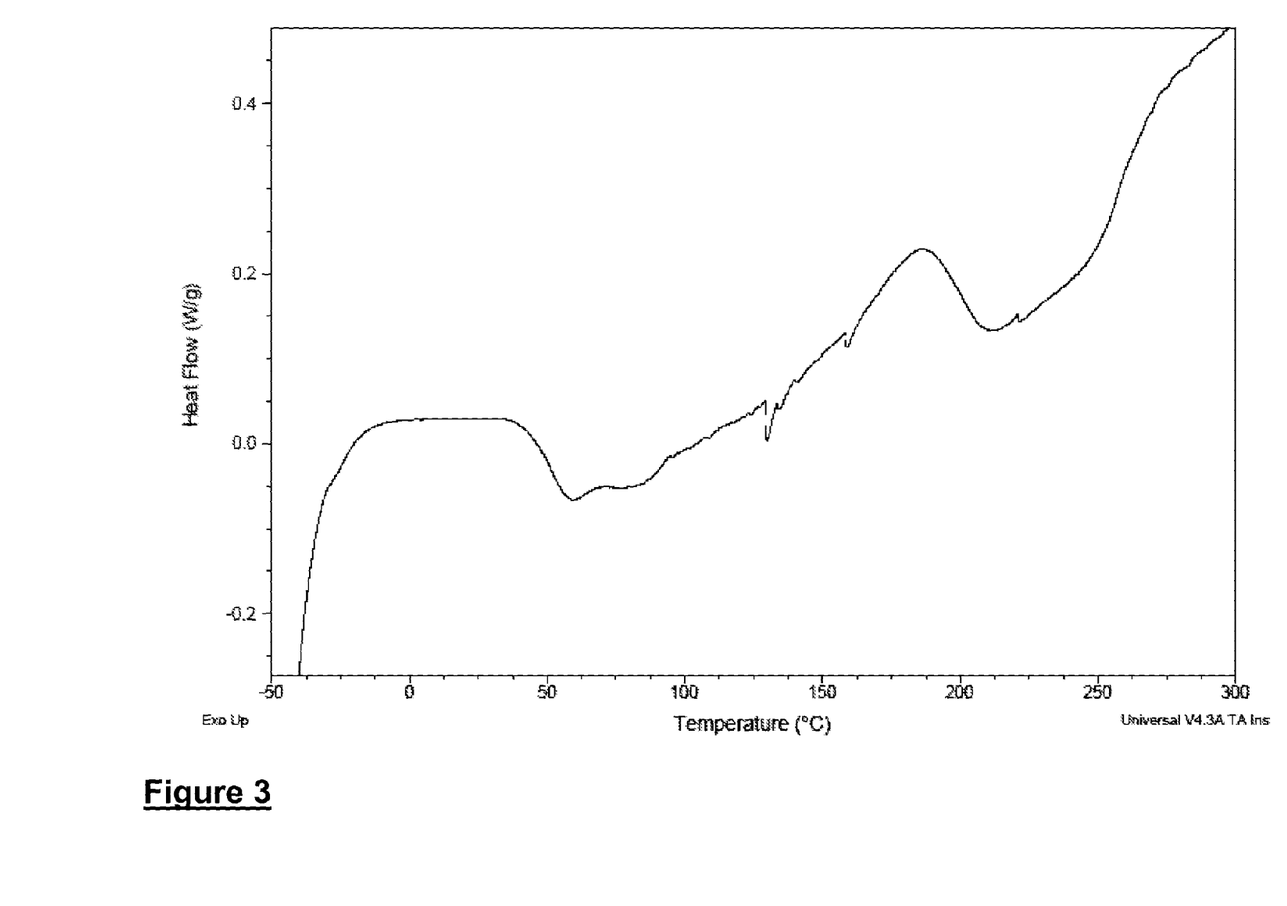
FIG. 3 shows the DSC thermogram for amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide.

Amorphous 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was also analysed by DSC, see FIG. 3.

Example 9

Chemical stability of amorphous versus crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide when exposed to high temperature/humidity for one week The stability of amorphous versus crystalline 5-cyano-3-methyl-pyridine-2-carboxylic acid [3-((3R,6R)-5-amino-3,6-dimethyl-6-trifluoromethyl-3,6-dihydro-2H-[1,4]oxazin-3-yl)-4-fluoro-phenyl]-amide was tested by exposing the amorphous or crystalline material to high temperature and/or humidity for one week. After storage at high temperature and/or humidity, bulk amorphous or crystalline material was sampled and dissolved in acetonitrile and the purity analysed in a Aquity UPLC from Waters using the following conditions:

| | |
|---|---|
| Separation column | Acquity UPLC BEH C18 (2.1 * 50 mm) |
| Mobile phase | A: water + 0.1% TFA B: ACN + 0.1% TFA |
| Gradient | 10 > 60 within 10 min; 60 for 1 min; 60 > 10 within 1 min |
| Flow | 0.4 ml/min |
| Column T° | 30° C. |
| Detection | 220 nm |

The results of this test are shown in Table 4.

TABLE 4

| Test conditions | Amorphous | Crystalline | |
|---|---|---|---|
| Temp/RH; Exposure Time | Purity-% | Purity-% | Solid State |
| RT; 0 | 96.4 | 98.7 | Crystalline |
| RT; one week | 96.3 | Not Tested | Not Tested |
| 40° C./75% RH; one week | Not Tested | 98.23 | Crystalline |
| 50° C.; one week | 91.6 | 98.05 | Crystalline |
| 80° C.; one week | 55.8 | 98.01 | Crystalline, Low† |

†= Lower peaks when measured by XRPD

The invention claimed is:
1. A crystalline form of the compound which has an X-ray powder diffraction pattern with at least one, two or three peaks having angle of refraction 2 theta (θ) values selected from 8.3, 9.0, 10.9, 12.9, 13.9, 15.4, 16.2, 17.1, 18.2, and 24.5° when measured using CuK$_\alpha$ radiation wherein said values are plus or minus 0.2° 2θ.

2. The crystalline form of the compound of claim 1 in substantially pure form.

3. The crystalline form of the compound of claim 1 which has an X-ray powder diffraction pattern substantially the same as the X-ray powder diffraction pattern shown in FIG. 1 when measured using CuK$_\alpha$ radiation.

4. A pharmaceutical composition comprising a crystalline form of the compound of claim 1 as an active pharmaceutical ingredient in association with at least one pharmaceutically acceptable carrier or diluent.

5. The pharmaceutical composition of claim 4 which further comprises a therapeutic agent or agents.

6. A pharmaceutical combination comprising a therapeutically effective amount of a crystalline form of the compound of claim 1 and a drug substance, for simultaneous or sequential administration.

7. A crystalline form of the compound according to claim 1 which has an X-ray powder diffraction pattern with at least one, two or three peaks having angle of refraction 2 theta (θ) values selected from 8.3, 9.0, 10.9, 12.9, 13.9, 15.4, 16.2, 17.1 and 18.2° when measured using CuK$_\alpha$ radiation, wherein said values are plus or minus 0.2° 2θ.

8. A crystalline form of the compound according to claim 1 which has an X-ray powder diffraction pattern with at least one, two or three peaks having angle of refraction 2 theta (θ) values selected from 8.3, 9.0, 10.9, 12.9, 13.9, 15.4, 16.2 and 17.1° when measured using CuK$_\alpha$ radiation, wherein said values are plus or minus 0.2° 2θ.

9. A crystalline form of the compound according to claim 1 which has an X-ray powder diffraction pattern with at least one, two or three peaks having angle of refraction 2 theta (θ) values selected from 8.3, 9.0, 10.9, 12.9, 13.9, 15.4 and 16.2° when measured using CuK$_\alpha$ radiation, wherein said values are plus or minus 0.2° 2θ.

* * * * *